United States Patent [19]
Clark, Jr.

[11] Patent Number: 5,824,703
[45] Date of Patent: *Oct. 20, 1998

[54] METHOD OF ASSISTING NORMAL BREATHING IN A MAMMAL HAVING A LUNG DISORDER

[75] Inventor: Leland C. Clark, Jr., Cincinnati, Ohio

[73] Assignee: Synthetic Blood International, Inc., Seattle, Wash.

[ * ] Notice: The term of this patent shall not extend beyond the expiration date of Pat. No. 5,674,913.

[21] Appl. No.: 777,399

[22] Filed: Dec. 27, 1996

Related U.S. Application Data

[63] Continuation of Ser. No. 439,590, May 12, 1995, abandoned, which is a continuation-in-part of Ser. No. 242,310, May 13, 1994, Pat. No. 5,674,913.

[51] Int. Cl.$^6$ .................................................. A61K 31/34
[52] U.S. Cl. ........................ 514/461; 514/723; 514/743; 514/746; 514/753; 514/756; 514/759
[58] Field of Search ..................................... 514/753, 461, 514/723, 743, 756, 746, 759

[56] References Cited

U.S. PATENT DOCUMENTS

| | | |
|---|---|---|
| 3,911,138 | 10/1975 | Clark, Jr. . |
| 4,173,654 | 11/1979 | Scherer . |
| 5,158,536 | 10/1992 | Sekins et al. . |
| 5,295,953 | 3/1994 | Richard et al. . |
| 5,300,528 | 4/1994 | Graybill et al. . |
| 5,437,272 | 8/1995 | Fuhrman . |

FOREIGN PATENT DOCUMENTS

| | | |
|---|---|---|
| 9103267 | 9/1989 | WIPO . |
| 9219300 | 9/1991 | WIPO . |
| 9219232 | 5/1992 | WIPO . |

OTHER PUBLICATIONS

Van Nostraud's Chemist's Dictionary, p. 518 1962.

Hoffman, R.E. et al., *Biomat., Art, Cells & Immob. Biotech.*, "Arterial Blood Gases and Brain Oxygen Availability Following Infusion of Intratracheal Fluorocarbon Neat Liquids," 20 (2–4), 1073–1073, ©1992 by Marcel Dekker, Inc.

Leach, C.L. et al., *Critical Care Medicine*, "Perfluorocarbon–associated gas exchange (partial liquid ventilation) in respiratory distress syndrome: A prospective, randomized, controlled study," vol. 21, No. 9, ©1993 by Williams & Wilkins.

Clark, L.C., Jr. et al., Biomat., Art, Cells & Immob. Biotech., "Response of the Rabbit Lung as a Criterion of Safety for Fluorocarbon Breathing and Blood Substitutes," 20 (2–4), 1085–1099, ©1992 by Marcel Dekker, Inc.

Tütüncü, A.S. et al., American Review of Respiratory Disease, "Comparison Ventilatory Support with Intratracheal Perfluorocarbon Administration and Conventional . . . Acute Respiratory Failure," vol. 148, pp. 785–792 (1993).

*Primary Examiner*—Rebecca Cook
*Attorney, Agent, or Firm*—Klein & Szekeres, LLP

[57] ABSTRACT

A method of assisting a mammal having a lung disorder to breathe ambient gas normally, i.e., without the assistance of a ventilator. The method includes providing an animal having a lung disorder, such as surfactant deficiency, stiff lung, or hyperinflated lung syndrome, and instilling a minimum effective dose of a perfluorochemical liquid or emulsion through the trachea for coating the alveolar sacs of a lung of the mammal. The preferred perfluorochemicals have a very low vapor pressure to avoid inducing hyperinflated lung syndrome and are supplied in a minimum effective dosage sufficient to coat the inner lung surfaces. The perfluorochemicals are permeable to the ambient gas and reside substantially permanently within the alveolar sacs without inducing hyperinflated lung syndrome. The liquid is instilled in an amount sufficient to enable the animal to breathe the ambient gas normally with $O_2/CO_2$ blood gas exchange. Effective coating of the lungs with a small (generally <0.1 ml/kg) dose of very low vapor pressure perfluorochemical is achieved through administration of an aqueous emulsion of the perfluorochemical or a mixture of the very low vapor pressure compound in a larger volume of a higher vapor pressure carrier perfluorochemical.

30 Claims, 4 Drawing Sheets

METHOD OF ASSISTING NORMAL BREATHING IN A MAMMAL HAVING A LUNG DISORDER

This is a continuation of application Ser. No. 08/439,590, filed May 12, 1995, abandoned, for A METHOD OF ASSISTING NORMAL BREATHING IN A MAMMAL HAVING A LUNG DISORDER, which is a continuation-in-part of U.S. application Ser. No. 08/242,310, filed May 13, 1994 now U.S. Pat. No. 5,674,913.

BACKGROUND OF THE INVENTION

1. Field of the Invention

This invention relates to the therapeutic use of perfluorochemicals in mechanically unassisted breathing in a mammal having a breathing difficulty caused by injury, lung surfactant deficiency, emphysema, hyperinflated lung or other stiff lung syndrome, respiratory distress syndrome, or other lung dysfunction to attain and sustain satisfactory pulmonary blood gas exchange for prolonged periods.

2. Description of Related Art

Various respiratory syndromes interfere with the ability of the lungs to adequately exchange gas with the atmosphere. These respiratory problems are a major cause of mortality and morbidity. Complex mechanical systems can be used to augment natural respiration, but such solutions are often unacceptable, as for adults who will not tolerate such an impediment to their mobility, or impractical, cumbersome, and excessively costly, as for premature infants. In some cases, mechanically-assisted respiration may actually cause serious damage even as it saves lives. Therefore, there has been considerable interest in novel methods of dealing with respiratory problems, particularly if these methods can limit or even eliminate mechanical breathing assistance.

Since circulating blood is the major route of gas exchange for most mammalian tissues, technologies used to augment or replace blood have been looked to for solutions to problems of respiratory gas exchange. Perfluorocyclocarbon liquids and emulsions containing particles of these perfluorocarbons have been shown to be useful as artificial bloods and perfusates for organs. Clark, U.S. Pat. No. 3,911,138 (Artificial Blood and Method for Supporting Oxygen Transport in Animals). Such perfluorocyclocarbons have been found to support life as intravascular $O_2/CO_2$ transport agents and as external respiration media. Emulsions containing emulsified particles of perfluorocyclocarbons have been infused intravenously into experimental animals and function as $O_2/CO_2$-carrying agents intravascularly. These emulsions have been proven to be useful blood substitutes, and experimental animals given these emulsions intravascularly survive and live normal lives afterwards.

Considerable work has been reported in connection with the use of perfluorochemicals to improve gas exchange in animals with respiratory distress syndrome (RDS) and other lung diseases, such as those involving lung surfactant deficiency, emphysema, or other types of lung injury or deterioration. One of the driving forces for this work has been the limited success and high cost of traditional lung surfactant replacement therapy. While surfactant replacement has been shown to improve gas exchange when used early in infant RDS, this therapy has met with only limited success in treating advanced infant RDS, adult RDS, and other diseases involving lung surfactant deficiency. Leach et al., *Critical Care Medicine*, 21(9): 1270–78 (1993).

One proposed alternative treatment for surfactant-deficient lung diseases is liquid ventilation. Liquid ventilation is a process in which the gaseous functional residual capacity of the lung is replaced by a perfluorochemical liquid, and gas exchange is accomplished by inspiration and expiration of tidal volumes of liquid. This liquid has $O_2$ added and $CO_2$ removed by an artificial membrane lung or by other means, such as bubbling with oxygen. Replacement of the gaseous functional residual capacity by the perfluorochemical liquid eliminates the alveolar air/fluid interface and also reduces surface or interfacial tension in the surfactant-deficient lungs.

Although liquid ventilation has been shown to improve gas exchange in premature lambs and premature human infants with respiratory distress syndrome, this form of treatment has several drawbacks. Liquid ventilation requires specialized apparatus to deliver and remove tidal volumes of liquid and to oxygenate and remove $CO_2$ from the liquid. Furthermore, the movement of liquid tidal volumes through the airway generates high viscous resistive forces, making normal or spontaneous liquid breathing very difficult or impossible.

More recently, a modified liquid ventilation technique known as perfluorocarbon-associated gas exchange (also called partial liquid ventilation) has been developed. Tütüncü et al., *American Review of Respiratory Disease,* 148: 785–92 (1993). In perfluorocarbon-associated gas exchange, a liquid functional residual capacity is maintained in the lung and tidal volumes of gas are delivered by a conventional mechanical ventilator. This technique benefits from the surface tension-reducing properties of perfluorochemical liquids, the low resistance of the airway to gas flow characteristic of gas ventilation, and the simplicity and familiarity of conventional ventilators. Perfluorocarbon-associated gas exchange has been shown to facilitate oxygenation and $CO_2$ removal and improve lung mechanics in premature lambs with respiratory distress syndrome and in adult New Zealand rabbits with induced respiratory distress syndrome. Leach et al.; Tütüncü et al.

PCT Application No. WO 92/19232 ('232) to Faithful and Weers describes this functional residual capacity technique. Although that application discusses the possibility of using any of a wide variety of perfluorocarbons, the primary thrust of the invention disclosed is the use of perfluorooctylbromide (PFOB) as the preferred compound. This compound was chosen because it displayed an unusual positive spreading coefficient, a property that the application discloses as being essential for optimal functioning.

The '232 application envisions maintaining a volume of fluorocarbon in the lung approximately equal to the functional residual capacity. The reference discloses that at least 0.1 ml of fluorocarbon per kilogram of bodyweight be used, with the quantity not to exceed 50 ml/kg. The actual dosages used experimentally were between 3 and 15 ml/kg. To some extent the volume of PFOB may be dictated by the compound's rather rapid rate of evaporation in that low volumes of PFOB will evaporate completely between readministrations of the compound.

While the technique of the '232 application avoids the problems associated with liquid tidal volumes found in liquid ventilation, it too has several limitations. Both techniques require a significant volume of perfluorochemical liquid in order to maintain a liquid functional residual capacity in the lung, and because evaporation of the perfluorochemical is high, even more perfluorochemical liquid is required. The considerable loss of fluorocarbon to the atmosphere is not entirely without air pollution consequences. Furthermore, the animal is unable to breathe normally under treatment, and requires the assistance of a mechanical ventilator.

An additional problem with the use of perfluorochemical liquids to assist breathing is that certain perfluorochemicals, such as perfluorodecalin, (and probably PFOB to some extent) produce hyperinflated lung syndrome. Clark et al., *Biomat., Art. Cells & Immob. Biotech.,* 20(2–4): 1073–99 (1992). Hyperinflated lung syndrome is a phenomenon in which the lungs fill the chest cavity and do not collapse, making breathing very difficult. Animals with the syndrome often appear cyanotic, have labored respiration, are in obvious respiratory distress, and often die within one to four days. On autopsy, the lungs appear pink and uninjured, as is normal, but do not collapse when the thorax is opened. The syndrome occurs after infusion of intratracheal neat liquids or intravenous emulsions of certain perfluorochemicals, and can be shown to be related to fluorocarbon vapor pressure.

SUMMARY OF THE INVENTION

This invention is directed to a method of assisting a mammalian subject having a lung disorder to breathe ambient gas normally, i.e., without the assistance of a mechanical ventilator.

This method involves several steps, including providing a mammal having a lung disorder for normal breathing of ambient gas. For example, animals or humans deficient in lung surfactant may be assisted in normal breathing of an ambient gas, such as atmospheric air. Also, animals or humans with hyperinflated lung syndrome may be assisted in normal breathing. Ambient gas may be any of a number of other gases such as, for example, pure oxygen, a mixture containing oxygen, anesthetic gases, vapors, and inert gases.

The method contemplates coating the inside surfaces of the lung with a very thin layer of a perfluorochemical rather than allowing any substantial lung volume to be liquid-filled. The perfluorochemical spreads over the lung surfaces, acting as a surfactant to ensure inflation of alveolar sacs. It is contemplated that only compounds with very low vapor pressures be employed, thereby allowing the thin coating of perfluorochemical to remain in the lung for an indefinite, but very long, period of time and ensuring that the therapy does not itself induce hyperinflation or other lung damage. Although the perfluorochemicals selected for use are generally inert and not known to cause any biological damage, using only a thin coating of perfluorochemical greatly reduces the required dosage, thereby limiting any possible long-term damage.

The method includes instilling a perfluorochemical liquid through the trachea for transport to the alveolar sacs of a lung of the animal by any of a number of different means, such as spraying, injecting, pouring, nebulization, and aerosolization. The perfluorochemical is permeable to the ambient gas and coats the insides of the alveolar sacs substantially permanently without inducing hyperinflated lung syndrome. Examples of a few of the perfluorochemicals that may be used include: perfluorotetramethylcyclohexane (AP-144), perfluorophenanthrene (Pf-phenanthrene), perfluoromethyldecalin, perfluorodimethylethylcyclohexane, perfluorodimethyldecalin, perfluorodiethyldecalin, perfluoromethyladamantane, perfluorodimethyladamantane, perfluoro-6,7-H-undec-6-ene, and mixtures thereof. Preferably, the perfluorochemical liquid will have a boiling point of at least about 150° C. at atmospheric conditions. Currently, the two most preferred compounds are perfluorophenanthrene and perfluorotetramethylcyclohexane. The method specifically avoids compounds containing bromine because of their environmental effects on atmospheric ozone and because of possible toxicity from bromide and free radicals possibly released by breakdown of the compound within the body.

The perfluorochemical liquids used may be in the form of a neat liquid or an aqueous emulsion. The goal is to coat the inner surfaces of the alveolar sacs of the lung. The dosing of perfluorochemical liquid is in a minimum amount effective to allow the animal to breathe the ambient gas with normal $O_2/CO_2$ blood gas exchange without filling a substantial volume of the lung. Preferably, the dosing will be less than about 0.1 ml of perfluorochemical/kg of bodyweight.

An important part of the present invention comprises methods to introduce such small effective amounts of perfluorochemical and yet still ensure adequate coating of the lungs. This coating is achieved either by applying the perfluorochemical as part of a mixture of a very low vapor pressure and a higher vapor pressure liquid perfluorochemical as a carrier, or as part of an aqueous emulsion.

In the case of the perfluorocarbon mixture, the very low vapor pressure compound is dissolved in an excess of a higher vapor pressure carrier liquid so that a convenient dose of between about 1 ml/kg and about 20 ml/kg can be instilled into the lung, ensuring complete coating of the lung. Within a relatively short time, the higher vapor pressure compound is lost through evaporation, leaving the desired thin effective coating of the very low vapor pressure fluorocarbon.

Higher vapor pressure perfluorocarbon liquids such as perfluorohexane (FC 72, 3M Corp.), perfluoro-2-butyltetrahydrofuran (FC 75, PCR/SCM), perfluoropolypropoxy ethers ($F(CF_3CFCF_2O)_2CHFCF_3$ (E2) and $F(CF_3CFCF_2O)_3CHFCF_3$ (E3), DuPont Corp.), perfluorotrimethylcyclohexane (AP-125, Air Products & Chemicals), perfluoro-5,6-H-dec-5-ene (F-44E, DuPont Corp.) and perfluorodecalin, cis and trans isomers (PP5) are useful carrier substances, as are other perfluorochemicals with a boiling point below about 140° C. These compounds can be used at low doses as solvents for the very low vapor pressure perfluorocarbons such that hyperinflation is not induced.

In addition, the present invention contemplates that a safe (either higher vapor pressure or very low vapor pressure) perfluorocarbon liquid can be instilled into lungs to redistribute or to remove a previously applied coating dose of a suitable very low vapor pressure perfluorocarbon liquid.

In the case of an aqueous emulsion, the small dose of the very low vapor pressure perfluorochemical is dispersed in an aqueous emulsion either by mechanical agitation and/or by use of an appropriate surfactant. Useful surfactants include Pluronic (polyoxylene) surfactants such as F68, XMO (perfluoroether surfactants) such as XMO-10 and XMO-20, bile acids, phospholipids, and even natural lung surfactant. Lipids, such as triglycerides, or other nonaqueous components may be added, as is well known in the art of preparing biologically compatible emulsions. The aqueous phase comprises a suitable physiologically compatible buffer such as Ringer's solution with bicarbonate and possibly osmotic and oncotic agents, such as glucose and proteins.

The emulsion is supplied in adequate quantities (between about 1 ml/kg and about 20 ml/kg bodyweight) to coat the lungs. Obviously, the dose of emulsion must not be so high as to significantly augment respiratory distress of the recipient. The aqueous phase is rapidly absorbed by the lung cells, leaving the desired coating of perfluorochemical. The emulsion can also be made using the above-described mixture of higher and very low vapor pressure perfluorochemicals, thereby increasing its oxygen carrying capacity and allowing larger amounts of the emulsion to be employed without increasing respiratory distress. The aqueous phase is absorbed and the higher vapor pressure perfluorochemical evaporates, thereby leaving an effective coating of very low vapor pressure perfluorochemical.

In the Detailed Description of the present invention the various mixtures and liquids are described as being instilled into lungs by an intratracheal route through a tracheotomy. It is to be understood that any other convenient methods of depositing the perfluorocarbon liquids, mixtures and emulsions into lungs, such as by spray or aerosol, are equally contemplated by the present invention.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Figure 1:
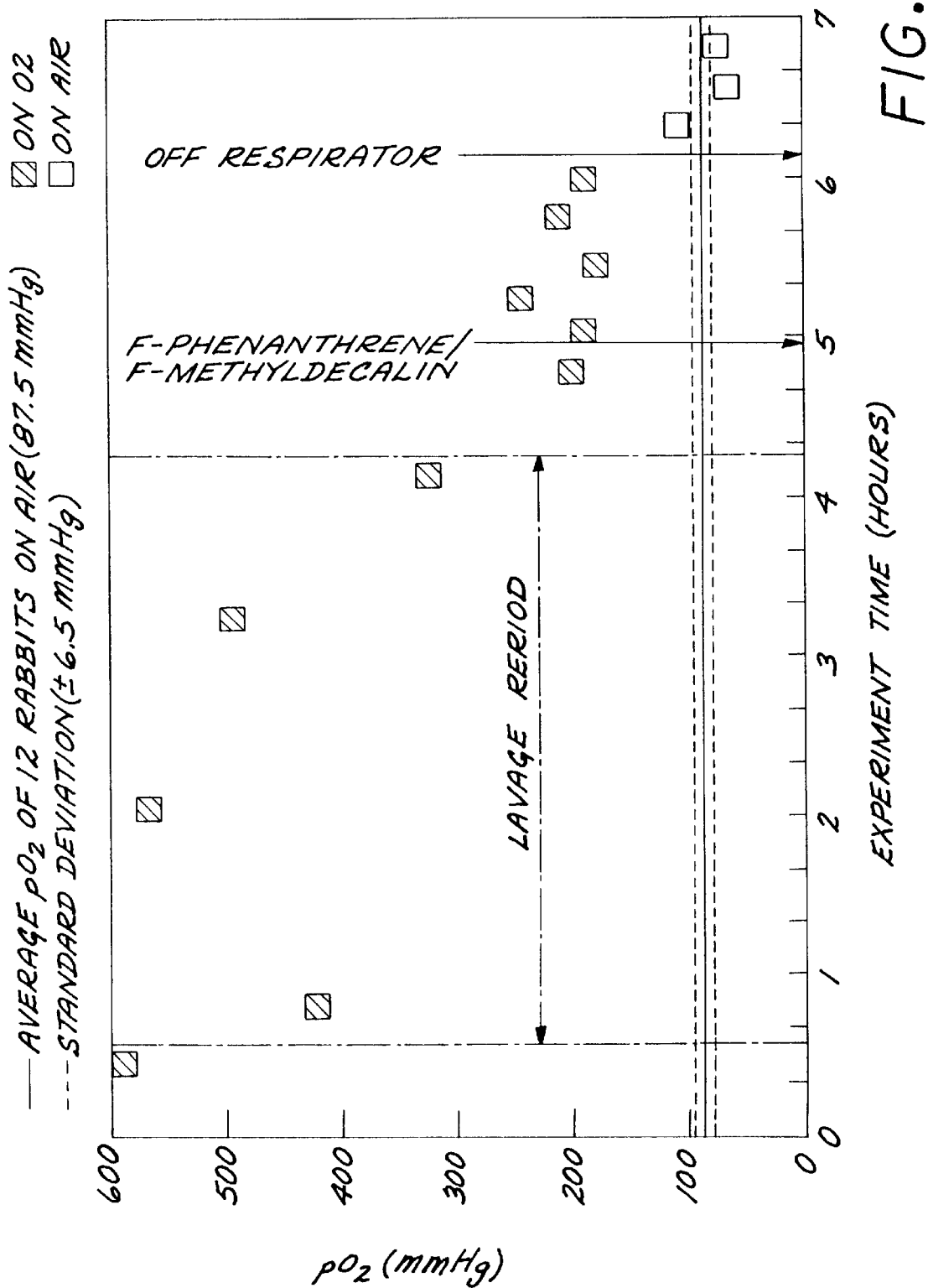
FIG. 1 is a graph showing arterial $pO_2$ in an adult white New Zealand rabbit, with respiratory distress syndrome, being assisted to breathe normally. The horizontal axis shows experiment time, and the vertical axis shows $pO_2$ expressed in mm Hg.

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a method of using a minimal lung coating of a very low pressure perfluorocarbon liquid to assist a mammal having a lung disorder to breathe ambient gas normally, i.e., without the mechanical assistance of a ventilator.

Perfluorochemicals, the subject chemicals of this application, have a number of extremely interesting properties which recommend them for medical use. Physiologically important gases, both oxygen and carbon dioxide, are extremely soluble in these compounds, hence the early and continuing interest in perfluorochemicals as safe substitutes for blood. The second characteristic that recommends perfluorochemical is their almost total chemical inertness. The compounds are virtually insoluble in water, and the absence of reactive protons in their molecular structures means that they exhibit little or no significant tissue affinity mediated by hydrogen bonds. At the same time, the presence of fluorine atoms renders the compounds lipophobic so they do not readily dissolve in the lipid bilayers of cell membranes. In addition, the low surface tension of most perfluorocarbon liquids enables the liquids to spread readily over lung tissue creating a thin effective coating and is especially desirable for the present invention.

Numerous experiments in using perfluorocarbon aqueous emulsions as blood substitutes have shown that the major fate of injected perfluorocarbons is loss by evaporation through the lungs and the surface of the skin. Prior to loss by evaporation many of the perfluorocarbon particles created through emulsification are captured by the phagocytic macrophages of the reticuloendothelial system. These cells then deposit the perfluorocarbon mainly in the liver, although some also goes to the spleen and bone marrow.

Although perfluorinated compounds are generally inert chemically, there is some concern that they might undergo enzymatic breakdown if they are retained for long periods in the body tissues. This concern is heightened in the case of bromine-containing perfluorocarbons, since enzymatic release of bromide would be particularly undesirable because the release of bromide ions in the tissue could be associated with the production of dangerous free radicals. As a consequence, selection of perfluorochemicals, especially those intended for artificial blood use, was initially thought to require a balance between high vapor pressure compounds, showing rapid evaporation with its attendant need for constant replenishment of the perfluorochemical, and low vapor pressure compounds showing excessive residency in the body. The high solubility of atmospheric gases in perfluorochemicals makes it virtually impossible to determine vapor pressure by the usual tests; therefore, boiling point has been used as a surrogate. At one time, the ideal compromise boiling point (vapor pressure) seemed to be with compounds like perfluorodecalin that boiled between 140° and 145° C.

Some years ago this Applicant discovered that in spite of the chemical inertness of perfluorocarbons, many of these compounds were capable of causing a distinctive type of lung damage. Normal mammalian lungs are flexible and elastic. During inhalation, muscles act on the chest wall and an internal partition called the diaphragm to create a partial vacuum in the chest cavity. Air is drawn into the flexible lungs, expanding them to fill part of the partial vacuum. In exhalation the process is reversed and air is expelled as the lung collapses. Normally, when the chest cavity is opened surgically, the lungs will collapse since they are no longer supported by a pressure differential between the chest cavity and the atmosphere. However, when an animal treated either intravenously or intratracheally with certain perfluorochemicals has its chest opened, its lungs fail to collapse. Instead, they remain stiff and extended, filling the chest cavity. At a gross level the damaged lungs resemble those of emphysema, which are also stiff and unable to respond to changes in chest cavity pressure.

This lung damage was termed Hyperinflated Lung Syndrome (HLS) and was found by the Applicant to be caused by perfluorocarbons of relatively high vapor pressures and to be suppressed by allowing the animal to breathe air containing vapors of the same perfluorocarbon which had been injected intravascularly. Apparently HLS is caused by the tendency of high vapor pressure perfluorocarbons to vaporize more rapidly than they can diffuse through the lung tissues.

As low levels of the compounds diffuse through the lung tissues, either from the blood towards the lumen of the lung in the case of intravascularly applied compounds, or from the lumen towards the blood in the case of intratracheally applied compounds, small bubbles form within the lung tissues as the fluorochemical's vapor pressure exceeds a certain critical value. The bubbles then become enlarged as they become filled with ambient blood and atmospheric gases in the proportions dictated by the Universal Gas Law in a process analogous to osmosis. That is, biological tissue is differentially permeable to various gases. The tissue is virtually impermeable to fluorocarbon vapor but very permeable to atmospheric gases. Thus, atmospheric gases diffuse into the bubbles until their partial pressures within the bubbles are equal to their partial pressures within the atmosphere (lumen of the lung). Filling the lumen of the lung with fluorocarbon vapor can reduce this process by lowering the partial pressures of the readily permeable atmospheric gases. The gas bubbles convert the normally flexible lung tissue into a relatively stiff bubble-filled tissue in much the same way that flexible sheets of plastic film are converted into stiffened sheets of bubble-wrap packing material. For additional information on hyperinflation, see Schott et al. "Proposed Mechanism of Pulmonary Gas Trapping Following Intravenous Perfluorocarbon Emulsion Administration," poster presented at the International Symposium on Blood Substitutes, Sheraton Hotel, San Diego, Calif. Mar. 16–20, 1993.

The HLS bubbles can be avoided by either decreasing the tendency of the perfluorochemical to vaporize (i.e. lower vapor pressure) or by using a compound that diffuses more rapidly through biological tissue so that the "osmotic" effect is reduced. The only practical approach is to use compounds with a sufficiently low vapor pressure. It now appears that only compounds with boiling points of about 150° C. and higher are likely to be free of the HLS hazard.

Two compounds presently preferred for this invention are perfluorophenanthrene with a boiling point of about 215° C. and perfluorotetramethylcyclohexane (AP-144) with a boiling point of about 150° C. Perfluorophenanthrene is expected to have a very long residence time in the lung because of its very low vapor pressure. This compound is already enjoying considerable success as a safe replacement for vitreous humor in eye surgery. Tests have shown that perfluorotetramethylcyclohexane has a sufficiently low vapor pressure to avoid any hyperinflation damage. However, its lung residence time is more in the range of days or weeks. Therefore, this compound can advantageously be used in mixtures as a carrier for perfluorophenanthrene and as a lavage to remove or redistribute perfluorophenanthrene.

The important and not necessarily obvious point is that while both intravascular perfluorocarbons (artificial blood) and intratracheally administered perfluorocarbons (the present invention) can cause HLS, the criteria for choosing ideal compounds are not the same for both applications. Since very little of the perfluorocarbon administered through the lung actually gets into the rest of the body due to poor solubility in and to poor diffusion through biological tissue, high boiling compounds that result in very long residency periods in the lung are safe and, in fact, preferred for intratracheal administration. Also, since there is rapid exchange of air from the lungs, some compounds with higher vapor pressures can be safely used, since, at the doses employed, these compound will have evaporated from the lung before sufficient perfluorocarbon material has diffused into the biological tissues to cause the formation of gas bubbles. Of course, such compounds would not be very useful for relieving RDS because they will disappear from the lungs in a manner of hours. These two competing properties are central to the present invention.

Having discussed the dangers of HLS and the criteria controlling the choice of perfluorochemicals in the present invention, one other property, namely the low surface tension of the perfluorocarbons, should be mentioned. As will be developed in more detail below, the major reason to add perfluorocarbons to lungs is to coat the alveolar sacs, thus allowing inflation of these sacs without any restriction due to lung surface sticking to lung surface. Normally, the lung surface is coated with a special native lung surfactant, but in certain disease states the native surfactant is insufficient to prevent sticking of lung tissue. If the lung surfaces are coated by an inert material such as a perfluorochemical that is soluble neither in water or lipid, sticking of the lung tissues can be prevented.

Although it is known that most liquid perfluorocarbons have very low surface tension, i.e. 20 mN/m or less at physiological temperatures, there has been some discussion of whether perfluorochemicals can adequately spread to coat the surface of a lung. Some workers have tried to derive "spreading coefficients" to justify the choice of one compound over another. In fact, this whole matter was dealt with in great detail in a research publication intended to measure the actual surface tension of a lung surface (S. Schurch, S., J. Goerke, and J. A. Clements, *Proc. Natl. Acad. Sci. USA*, 73: 4698–4702 (1976)). Those workers discovered that the exact surface tension of the lung surface of rat lungs varied from about 9 mN/m to about 20 mN/m at different lung inflations ranging from 62% to 87% of Total Lung Capacity.

In other words, deflated lungs most in need of surfactant protection showed the lowest surface tension, i.e. the most efficient surfactant effect. Furthermore, this work demonstrated that the perfluorocarbon liquid would spread out into a thin lens of fluid whenever the lung surface tension exceeded that of the perfluorocarbon. Surfactant deficient lungs are known to have surface tensions of 30 mN/m or greater, a figure that is higher than the surface tensions of any of the likely candidate perfluorochemicals. Thus, if the perfluorochemicals are evenly distributed in the lungs, they will automatically spread out and coat the lungs if the lungs are deficient in native surfactant. If there is adequate surfactant present initially or a later time so that the lung surface tension falls below that of the perfluorocarbon, the perfluorocarbon will presumably round up into tiny droplets until and if the lung surface tension again becomes high.

For example, animals or humans deficient in lung surfactant, having hyperinflated lung syndrome or some other lung defect, may be assisted in normal breathing of ambient atmospheric gases. Ambient gases may be any of a number of gases including, for example, pure oxygen, a mixture containing oxygen, anesthetic gases, vapors, and inert gases.

A perfluorochemical liquid is instilled through the trachea for coating the finer spaces of the lungs, the alveolar sacs, of the animal, by any of a number of different means, such as spraying, pouring, etc. The perfluorochemical is permeable to the ambient gas and resides within the alveoli or the alveolar sacs coating the lung surface substantially permanently without inducing hyperinflated lung syndrome. The term "substantially permanently" refers to significant periods of time on the order of days, weeks, months, or even years, depending upon the extent of assistance needed. The residence time in the lung is mainly related to the vapor pressure of the fluorocarbon.

As already explained, perfluorochemicals are used because of their abilities as $O_2/CO_2$ transport agents, as well as their chemical and biological inertness, their ability to "wet" and spread in a thin film or layer on the inside of the lungs, and their low surface tension. Perfluorocarbons readily dissolve large amounts of $O_2$ and $CO_2$, and are so chemically inert that they have no adverse pharmacological activity. The perfluorochemical liquid used should have a vapor pressure low enough to avoid pulmonary side effects such as hyperinflated lung syndrome, and low enough to allow the liquid to remain in the alveolar sacs for a sufficient period of time.

With respect to this invention, the preferred perfluorochemical liquid has a boiling point of at least about 150° C. at atmospheric conditions (standard pressure, 760 mm Hg). Such a perfluorochemical may be selected to reside in the lung for days, weeks, months, and even years, depending upon the perfluorochemical selected. Any of a number of different perfluorocarbons may be used, including liquids such as: perfluorophenanthrene, perfluorotetramethylcyclohexane, perfluoromethyldecalin, perfluorodimethylethylcyclohexane, perfluorodimethyldecalin, perfluorodiethyldecalin, perfluoromethyladamantane, perfluorodimethyladamantane, perfluoro-6,7-H-undec-6-ene, and mixtures thereof with perfluorotetramethylcyclohexane and perfluorophenanthrene currently being the very low vapor pressure compounds of choice.

The perfluorochemical liquids used may be in the form of a neat liquid, generally being a mixture of a higher vapor pressure carrier and a very low vapor pressure "coating" molecule, or an aqueous emulsion. When an oil-in-water emulsion is used, the water part of the emulsion and the emulsifier are absorbed and the fluorocarbon part is "filtered out" and deposited on the inner surface of the alveoli, possibly as particles which spread when the lung surface tension becomes higher than that of the perfluorochemical.

The liquid is added in an amount sufficient to enable the animal to breathe the ambient gas with normal $O_2/CO_2$ blood gas exchange. One of the reasons the animal is able to breathe normally is that this invention uses relatively small doses of the perfluorochemical liquid. Existing therapies such as liquid ventilation and perfluorocarbon-associated gas exchange (partial liquid mechanical ventilation) call for a very large dose of perfluorochemical liquid, a dose equivalent to at least normal functional residual capacity of the lung. In the premature lamb, this volume translates to 30 ml/kg, and in the adult New Zealand rabbit, this volume typically corresponds to about 18 ml/kg. Leach et al., *Critical Care Medicine,* 21(9): 1270–78 (1993); Tütüncü et al., *American Review of Respiratory Disease,* 148: 785–92 (1993). With liquid ventilation, the total dose of perfluorochemical liquid also includes the liquid tidal volume. The inventive method, however, calls for a substantially lower dose of perfluorochemical liquid, enough to merely coat the surface of the alveolar sacs as opposed to filling a significant part of the functional residual volume of the lungs. In this invention, the dosing may be in any amount sufficient to allow the animal to breathe normally and, in the preferred form of the invention, the dosing typically is from about 1 ml of solution/kg bodyweight to about 10 ml/kg of either a perfluorocarbon mixture or emulsion. The effective concentration of very low vapor pressure perfluorocarbon is low, preferably below 0.1 ml/kg, with the remainder of the solution supplying bulk to ensure distribution of the very low vapor pressure perfluorocarbon.

The following examples demonstrate several aspects of the inventive method of assisting an animal having a lung disorder to breathe ambient gas normally. The initial examples, while demonstrating the effectiveness of perfluorochemicals, generally employ a larger amount of perfluorocarbon than is preferred so that any toxic effects, as well as residual levels of the compound, can be more readily detected. After long-term safety has been demonstrated, later examples show the efficacy of the preferred minimal effective dose of very low vapor pressure perfluorocarbon.

EXAMPLE 1

Example 1 shows an animal with respiratory distress syndrome being assisted by the inventive method to breathe normally; that is, without the assistance of a mechanical ventilator.

A normal white adult New Zealand rabbit was anesthetized and an Abbocath plastic cannula was placed in an ear artery for blood sampling. A silicone rubber (Silastic) cannula tube was secured in the trachea via a cut-down on the trachea and the animal was connected to a Harvard respirator that was connected to an oxygen supply. The stroke volume and rate were adjusted as judged appropriate for an animal of this size. Connections were made so that the oxygen pressure could not exceed 15 cm of water. A very slight negative pressure was applied to the outlet valve of the respirator in order to assure maximum tidal volume. The ventilator was adjusted to maintain a low-side arterial $CO_2$ tension. Heparinized arterial blood samples were collected anaerobically and analyzed immediately for blood gas tensions and pH. Additional analyses for blood lactate, glucose, and hematocrit were also performed.

The lungs of the rabbit were lavaged with successive volumes of isotonic saline in order to remove natural lung surfactant. The appearance of the lavaged liquid and the drop in arterial $pO_2$ were the main criteria used to judge the removal of surfactant (see FIG. 1). The ventilator was disconnected while the saline lavage fluid was slowly injected and withdrawn. The lavage process was continued until the $pO_2$ dropped a little below 200 Torr, with the animal breathing 100% oxygen. FIG. 1 shows the progressive drop in arterial oxygen tension as lung surfactant was washed out with saline.

While oxygen was flowing into the tracheal cannula, the perfluorochemical liquid was infused (shown by vertical arrow in FIG. 1). 3 ml/kg (9.6 ml) of a 1:1 mixture of perfluorophenanthrene and perfluoromethyldecalin, two low vapor pressure perfluorocarbons, were given intratracheally. After the fluorocarbon was administered and mechanical ventilation continued, the arterial $pO_2$ was well maintained (FIG. 1).

When the tracheal tube was removed and the mechanical ventilator was turned off, the animal spontaneously breathed air. In fact, once the Harvard ventilator was disconnected from the rabbit, the animal responded by licking and drinking water and by sitting upright. Pulmonary function was maintained as shown by the arterial $pO_2$, which remained at a level near the average $pO_2$ for healthy rabbits breathing air (FIG. 1).

Laboratory Method for Examples 2–5

Several normal young adult white New Zealand rabbits, free of Pasteurella and *Encephalitozoon cuniculi,* were anesthetized with intravenous ketamine at a dose of 20 mg/kg. For each animal, using sterile techniques, a silicone rubber (Silastic) tracheal cannula was placed and secured following a midline incision of the neck. The silicone rubber catheter had a snug fit to the inner diameter of the trachea. Oxygen was given through the cannula, which was fitted with a funnel consisting of the barrel of a 12-ml plastic syringe, while biological grade perfluorophenanthrene was slowly poured into the funnel. The perfluorocarbon liquid had been forced through a 0.22-micron filter to remove any particles before use.

During infusion of the perfluorocarbon liquid, the head and shoulders of each rabbit were somewhat elevated, and no sign of distress, such as choking or struggling, was observed. Following the infusion, the tracheal incision was closed with two stitches of 5-0 silk, a square of Gelfoam™ was placed over the closed tracheal incision, and the muscle and skin were sutured using 2-0 silk. Recovery from the anesthesia was uneventful and the animals were awake and appeared normal within an hour after the infusion. The rabbits were maintained under daily observation until they were sacrificed using an intravenous overdose of sodium pentobarbital.

Blood measurements for pH, $pO_2$, $pCO_2$, hematocrit, glucose, and lactate were performed in the laboratory directly after collecting the blood. Gas chromatographic analysis for fluorocarbons in breath, blood, and tissues was conducted using methods for analysis of air or of head space developed in this laboratory. The gas chromatograph used was a Hewlett-Packard Model 5880A, and the column was ⅛-inch×20-foot stainless steel, packed with 20% SE-30 on 80/100 Chromasorb WAW. The carrier gas was 5% methane and 95% argon.

EXAMPLE 2

Example 2 demonstrates that perfluorophenanthrene remains in the lung several months after installation into the alveolar sacs. A quantity of perfluorocarbon in excess of that amount required to merely coat the lung surface was used to ensure a detectable residual after several months.

Table 1 shows the amount of perfluorophenanthrene in the blood and lungs several months after intratracheal administration of the perfluorochemical. Some of the rabbits received a 1:1 mixture of perfluorophenanthrene and perfluorooctylbromide (PFOB), as shown in Table 1, in which case PFOB values are shown in parentheses. The PFOB was given in order to examine intrapulmonary distribution by X-ray. For rabbits receiving the mixture, one-half of the dose shown in Table 1 was perfluorophenanthrene, while the other half was PFOB.

TABLE 1

Analysis of Blood and Lung Tissue at Autopsy for Perfluorophenanthrene Content by Gas Chromatography

| Rabbit | Dose cc/kg | Compounds | Months Post-Infusion | Blood pl/ml | Lung pl/gm |
|---|---|---|---|---|---|
| 328 | 2.0 | Pf-phenanthrene | 7.2 | 183 | 13,239 |
| 333 | 2.0 | 1:1 Pf-phenanthrene, PFOB | 5.6 | 466 (4.34) | 804,115 (171) |
| 334 | 6.0 | 1:1 Pf-phenanthrene, PFOB | 8.9 | 214 (1.78) | 2,352,356 (408) |
| 336 | 6.0 | 1:1 Pf-phenanthrene, PFOB | 14.1 | 398 (3.15) | 226,396 (57.6) |

As can be seen from Table 1, the amount of perfluorophenanthrene is much greater in the lungs than in the blood for each rabbit analyzed. The higher values for lung tissue show that the bulk of the perfluorophenanthrene remains in the lungs post-administration. Also, the low values for PFOB show how the PFOB almost entirely evaporates, leaving the perfluorophenanthrene.

EXAMPLE 3

Example 3 shows that the physiological response to breathing air, oxygen, and carbogen (95% oxygen and 5% carbon dioxide) is essentially normal during a nine-month period after receiving intratracheal perfluorophenanthrene, and that neither the brain nor lung is damaged by the injection of fluorocarbon liquid through the trachea.

Three weeks before the tracheal infusion of perfluorophenanthrene, a 2.02-kg young adult female rabbit was anesthetized with intravenous sodium pentobarbital, and bilateral platinum voltammetric electrodes were implanted in the cerebral cortex and bilateral silver wire electrodes were implanted subcutaneously and allowed to heal. A recording of brain $aO_2$ (cerebrocortical oxygen availability) and other electrochemophysiological measurements were made on this animal previous to the administration of the perfluorophenanthrene liquid. At the time of tracheal infusion, the rabbit weighed 2.9 kg and received 11.6 ml of liquid.

Figure 2:
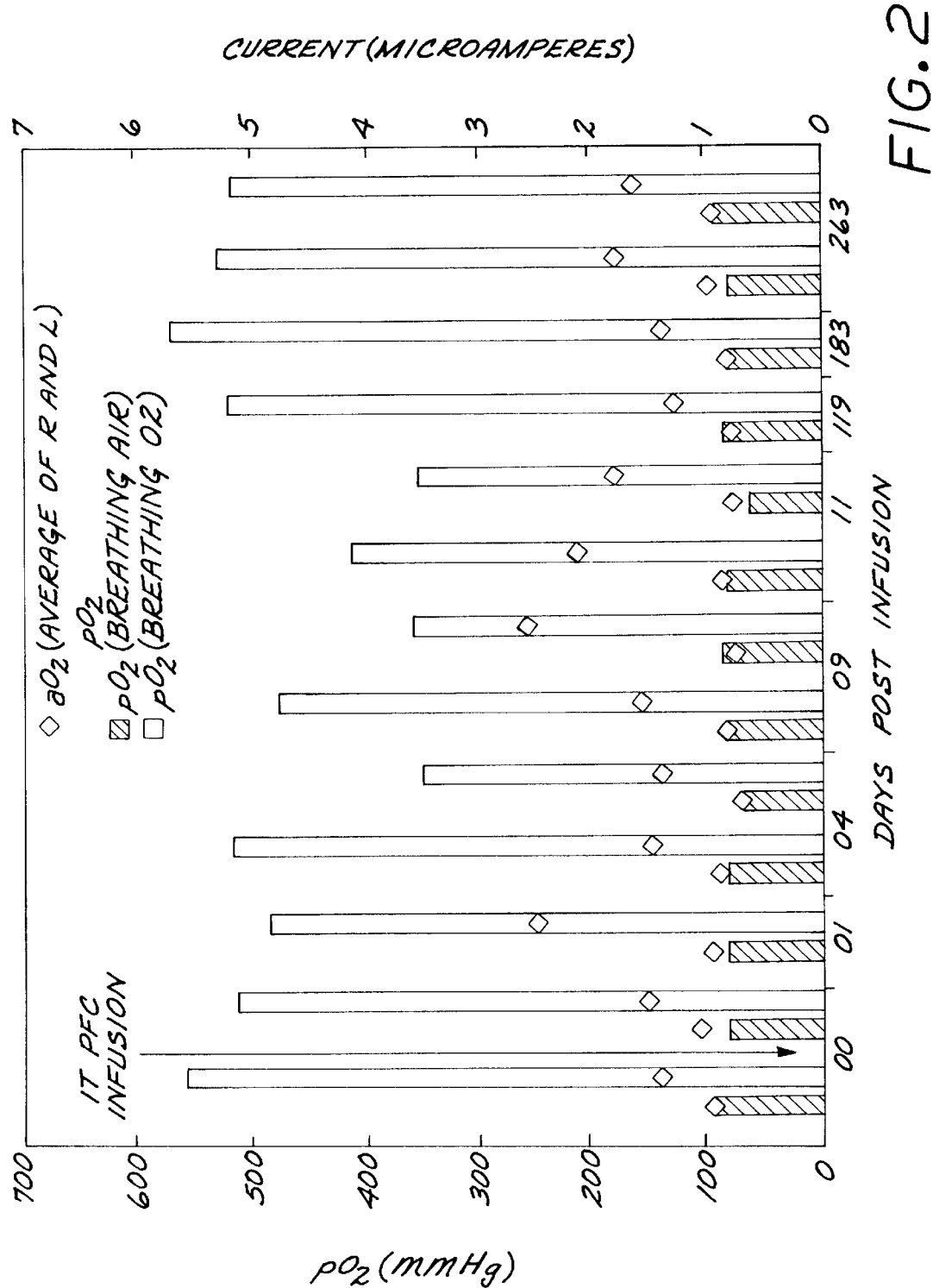
FIG. 2 is a graph showing arterial $pO_2$ and brain $aO_2$ oxygen current in a normal adult white New Zealand rabbit over a nine-month period following intratracheal infusion of perfluorophenanthrene. The horizontal axis shows days pre- and post-infusion, and the vertical axis shows $pO_2$ expressed in mm Hg, as well as $aO_2$ expressed in microamperes.
Figure 3:
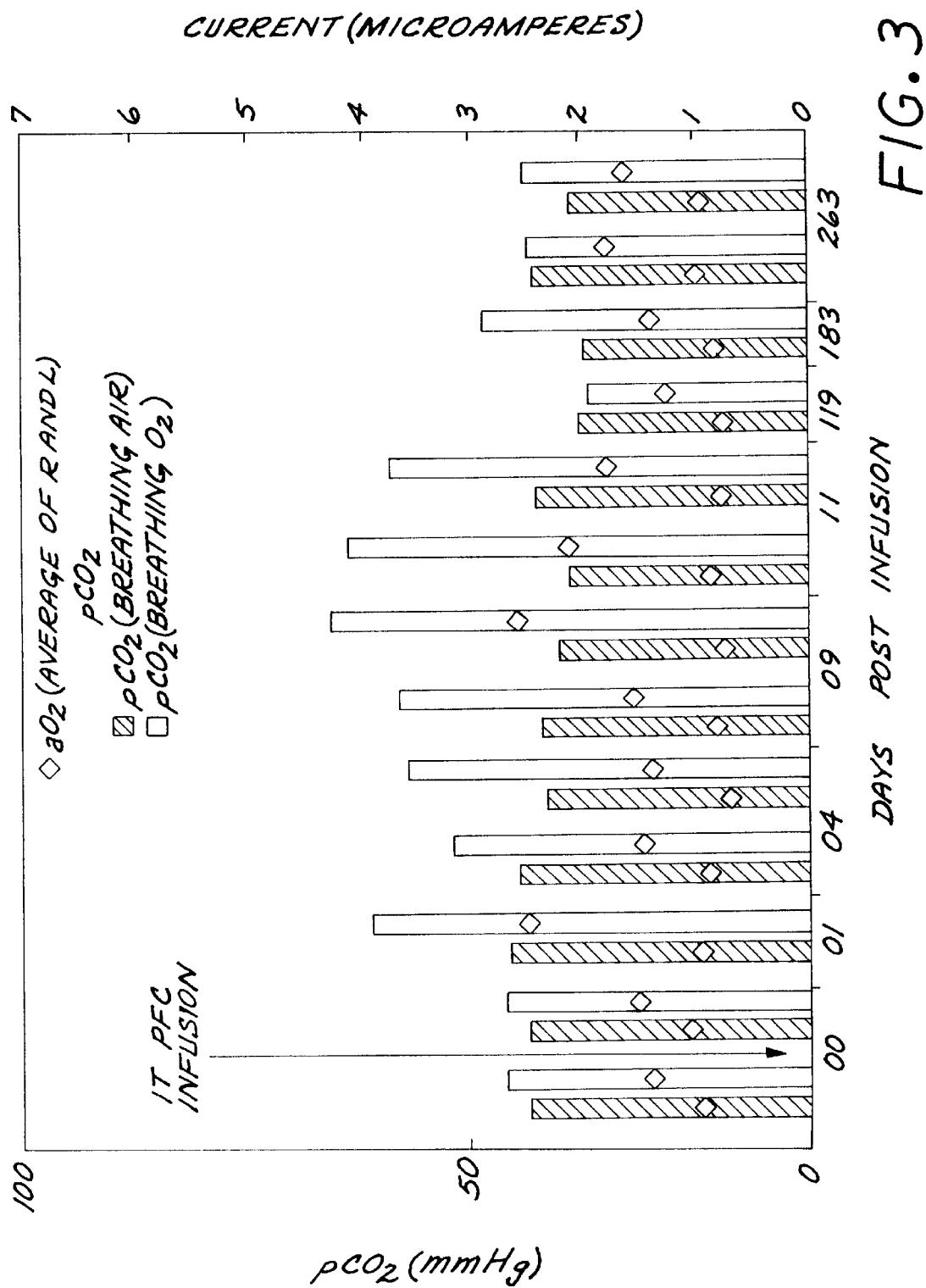
FIG. 3 is a graph showing arterial $pCO_2$ and brain $aO_2$ oxygen current in a normal adult white New Zealand rabbit over a nine-month period following intratracheal infusion of perfluorophenanthrene. The horizontal axis shows days pre- and post-infusion, and the vertical axis shows $pCO_2$ expressed in mm Hg, as well as $aO_2$ expressed in microamperes.

Arterial blood gas and brain $aO_2$ electrode current measurements were made routinely for approximately nine months after infusion of perfluorophenanthrene. Tables 2 and 3 show blood values immediately before and immediately after infusion. FIG. 2 shows $pO_2$ and brain $aO_2$ oxygen current values, and FIG. 3 illustrates $pCO_2$ and brain $aO_2$ oxygen current values over the nine-month period. These values remain relatively constant over the life of the rabbit.

Nine months after administration of the fluorocarbon liquid, the rabbit was killed by sodium pentobarbital overdose. At autopsy, the lung showed no sign of pulmonary damage or hyperinflation.

TABLE 2

Arterial Blood Values Just Before Intratracheal Fluorocarbon Liquid Infusion

|  | Air | Oxygen | Carbogen |
|---|---|---|---|
| pH | 7.25 | 7.30 | 7.24 |
| $pCO_2$, mm Hg | 35.1 | 36.2 | 38.5 |
| $pO_2$, mm Hg | 92.3 | 613.0 | 561.2 |
| hematocrit, % | 32.5 | — | — |

TABLE 3

Arterial Blood Values One Hour After Intratracheal Fluorocarbon Liquid Infusion

|  | Air | Oxygen | Carbogen |
|---|---|---|---|
| pH | 7.29 | 7.22 | 7.18 |
| $pCO_2$, mm Hg | 35.1 | 38.2 | 50.4 |
| $pO_2$, mm Hg | 80.0 | 513.0 | 554.3 |
| hematocrit, % | 30.3 | — | — |

EXAMPLE 4

Example 4 demonstrates that the physiological response to breathing air, oxygen, and carbogen (5% oxygen and 95% carbon dioxide) is essentially normal 20.5 months after infusion of perfluorophenanthrene.

A 1.84-kg young adult female rabbit was prepared for fluorocarbon administration according to the laboratory method described above, received 3.9 ml of perfluorophenanthrene (2 ml/kg) intratracheally, and was monitored for the next 20.5 months. Arterial blood values at month 15.5 and month 20.5 are shown in Table 4 and Table 5, respectively, and are relatively constant over tine. At autopsy, the lung appeared normal, and there was no sign of pulmonary damage or hyperinflation.

TABLE 4

Arterial Blood Values 15.5 Months After Intratracheal Infusion

|  | Air | Oxygen |
|---|---|---|
| pH | 7.28 | 7.30 |
| pCO$_2$, mm Hg | 35.3 | 36.2 |
| pO$_2$, mm Hg | 78.0 | 613 |
| glucose, mg % | 90.0 | — |
| lactate, mM | 0.6 | — |
| hematocrit, % | 36 | — |

TABLE 5

Arterial Blood Values 20.5 Months After Intratracheal Infusion

|  | Air | Oxygen | Carbogen |
|---|---|---|---|
| pH | 7.31 | 7.32 | 7.3 |
| pCO$_2$, mm Hg | 33.5 | 35.6 | 39.4 |
| pO$_2$, mm Hg | 81.8 | 574.0 | 596.0 |
| glucose, mg % | 91.5 | 86.0 | 76.5 |
| lactate, mM | 0.35 | 0.35 | 0.3 |
| hematocrit, % | 37 | — | — |

EXAMPLE 5

Example 5 shows an animal with perfluorodecalin-induced HLS being assisted by the inventive method to breathe normally; that is, without the assistance of a mechanical ventilator.

A healthy adult white New Zealand rabbit was given an intravenous dose of 10 ml/kg (26.6 ml) of a 10% by volume emulsion of perfluorodecalin in Pluronic F-68 surfactant (a polyoxylene surfactant), in order to induce HLS. This dose is known to induce maximum lung inflation in one day. One day after the emulsion was given, an intratracheal infusion of 10.5 ml perfluorophenanthrene neat liquid was made, according to the standard laboratory method described above. The animal was not placed on a mechanical respirator at any time during the experiment.

On autopsy, the lungs were examined by several trained observers and rated on a scale of 1 to 5, with 1 being the maximum inflation and 5 being a normal collapsed lung with no inflation. Without the perfluorophenanthrene infusion, the lungs would have had a rating of 1 at this time. And, in fact, a control rabbit given the same dose of perfluorodecalin emulsion at the same time as the perfluorophenanthrene-treated rabbit, and sacrificed at the same time, did have a lung rating of 1. However, the hyperinflated lung syndrome rabbit subsequently treated with perfluorophenanthrene had an average lung rating of 3.25 on autopsy.

Figure 4:
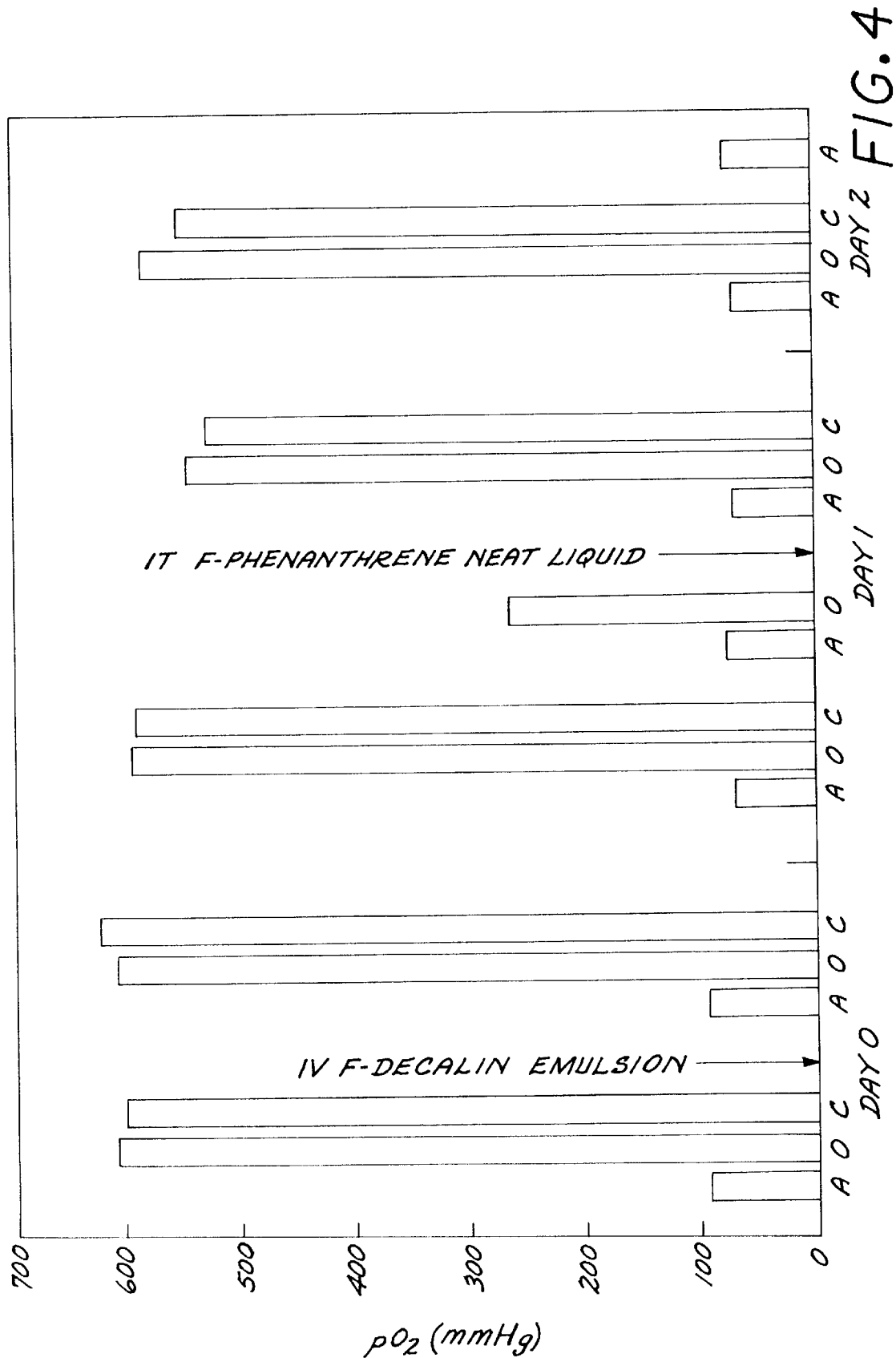
FIG. 4 is a graph showing arterial $pO_2$ in an adult white New Zealand rabbit, with perfluorodecalin-induced hyperinflated lung syndrome, being assisted to breathe normally. The horizontal axis shows arterial blood samples taken over time, with the animal breathing air (A), oxygen (O), or carbogen (C) (95% $O_2$/5% $CO_2$), and the vertical axis shows $pO_2$ expressed in mm Hg.

Arterial blood gas values for this animal over the duration of the experiment are shown in FIG. 4. The horizontal axis time line is divided into three days, and the intravenous (IV) administration of perfluorodecalin emulsion and intratracheal (IT) administration of perfluorophenanthrene are shown by the first and second arrows, respectively.

The pO$_2$ over time further illustrates the animal being assisted to breathe ambient gas normally with the intratracheal instillation of perfluorophenanthrene, following perfluorodecalin-induced lung syndrome. The lung disorder is particularly evident in the third data cluster following IV perfluorodecalin administration. The extraordinarily low pO$_2$ while the animal is breathing oxygen (O) shows poor O$_2$/CO$_2$ blood gas exchange typical of the lung disorder. However, shortly after the IT perfluorophenanthrene administration, the O$_2$/CO$_2$ transport across the membrane is greatly improved, as evidenced by the higher pO$_2$.

EXAMPLE 6

Procedure Used For Depositing a Low Dose of Low Vapor Pressure Perfluorocarbon in the Lungs of a Rabbit An adult female white New Zealand rabbit was anesthetized with sodium pentobarbital and the trachea exposed by an incision in the skin. A silicone rubber tube was selected to fit the inner diameter of the trachea and inserted through an incision in the trachea. The tube was anchored in place with a temporary ligature. The rabbit breathed 100% oxygen throughout.

Two milliliters per kilogram of a water-based emulsion containing 1 v/v% perfluorophenanthrene and 0.1 v/v% XMO-10, a perfluoroether surfactant manufactured by Allied Chemical having the general chemical formula (CF$_3$)$_2$—CFO—(CF$_2$)$_3$—CONH—(CH$_2$)$_3$—NO—(CH$_3$)$_2$ was given via a small plastic funnel connected to the tracheal cannula. This is equivalent to 0.02 ml of perfluorophenanthrene (AP-215, Air Products & Chemicals, high purity) per kg bodyweight. The XMO-10 surfactant had been previously identified as one of the few fluorinated surfactants capable of readily emulsifying liquid perfluorocarbons and yet being incapable of hemolyzing red blood cells at the effective concentration. The aqueous emulsion is intended to spread the perfluorocarbon evenly through the lungs of the rabbit. Then the water and the XMO-10 surfactant are absorbed by the lung tissue, leaving the perfluorophenanthrene to coat the lung surfaces. The XMO-10 is readily secreted by the kidneys without undergoing any chemical alterations.

The entire procedure was uneventful and recovery of the rabbit was prompt and complete. Arterial blood samples were analyzed for blood gases and pH at 1, 2, 4, and 30 days postinfusion while the animal was first breathing air and then oxygen. The pCO$_2$ readings ranged from 29.7 to 38.0 torr. The arterial pO$_2$ taken while the animal was breathing air and then oxygen were 93.5, 531; 85.5, 513; 86.0, 586 and, on day 30 (only on air), 94.0. The pH range for all samples was 7.29 to 7.35. All of these values are regarded as normal for a healthy animal.

The animal was sacrificed by lethal injection 347 days after the infusion and the lungs, which appeared normal on necropsy, were removed and refrigerated until analyzed by gas chromatography and electron capture detection for fluorocarbon content. Samples of lung were placed in sealed borosilicate glass bottles and the head space was analyzed after the samples were heated by microwave and allowed to cool. The results of this analysis are shown in Table 6.

TABLE 6

Perfluorophenanthrene Content of Lungs of Rabbit
Given 0.02 ml of Perfluorophenanthrene in
Emulsion Form 347 Days Previously

| Lung Samples from Lobes as Shown | Pf-Phenanthrene Content in Picoliters per Gram (Average) |
|---|---|
| Right superior | 91.3 |
| Right median | 223.0 |
| Right inferior | 127.0 |
| Post caval | 72.4 |
| Left superior | 91.2 |
| Left inferior | 167.0 |

EXAMPLE 7

Lavage of the Lung with a Safe Higher Vapor Pressure Fluorocarbon Liquid to Remove or Redistribute a Very Low Vapor Pressure Perfluorocarbon Since the very low vapor pressure perfluorocarbons of the present invention may remain in the lung substantially permanently, it is desirable to have a safe method to remove or redistribute them.

A healthy young adult Sprague-Dawley female rat weighing 200 g was anesthetized with a mixture of ketamine and xylazine and a plastic cannula was inserted into the trachea. A dose of 20 microliters (0.1 mg/kg bodyweight) of perfluorophenanthrene (AP-215) was administered and the rat allowed to remain anesthetized for one hour while breathing oxygen. Supplemental anesthetic was given as needed.

The lung was then lavaged with 1.2 milliliters (6 ml/kg bodyweight) of perfluorotetramethylcyclohexane (AP-144). The recovered perfluorocarbon was analyzed by electron capture gas chromatography. The perfluorophenanthrene peaks were readily visible (retention times: 9.06 and 9.43 minutes) after the perfluorotetramethylcyclohexane (retention time 3.86 minutes). The process was repeated with an additional 2 milliliters (10 ml/kg) of perfluorotetramethylcyclohexane and again perfluorophenanthrene was found in the fluorocarbon removed from the lung.

As explained earlier, perfluorotetramethylcyclohexane has a sufficiently low vapor pressure to be entirely safe although its residency time is not as long as even lower vapor pressure compounds. Therefore, it is ideal for redistributing or removing extremely persistent perfluorocarbons such as perfluorophenanthrene. The residual perfluorotetramethylcyclohexane itself will have essentially all evaporated within a few days. This procedure can also be performed using a higher vapor pressure perfluorocarbon such as perfluoro-2-butyltetrahydrofuran which will largely disappear from the lungs within a few hours.

EXAMPLE 8

The Effectiveness of Perfluorocarbon Mixture Coating

As mentioned and demonstrated above, very low vapor pressure perfluorocarbons can effectively coat lung surfaces, providing relief from respiratory difficulties without inducing further lung damage. Example 6 demonstrated an emulsion-based method of introducing a very small, lung coating minimum effective dose of very low vapor pressure perfluorocarbon. This example demonstrates the use of a mixture between low and higher vapor pressure perfluorocarbons as a vehicle to deliver a very small, lung coating dose of a very low vapor pressure perfluorocarbon.

Two young adult female Sprague-Dawley rats were anesthetized with a mixture of ketamine and xylazine, and a tracheal cannula of polyethylene tubing was inserted into the trachea via a tracheotomy. The rats breathed 100% oxygen throughout the procedure and maintained a steady, even respiratory rate.

Respiratory distress was induced through the removal of native lung surfactant by bronchoalveolar lavage using warm, oxygen-saturated saline. Lavage resulted in immediate irregular and uneven respiration with the rats appearing somewhat cyanotic.

After five minutes without apparent improvement, 6 ml/kg of 0.01 v/v% of perfluorophenanthrene (AP-215, Air Products & Chemicals) in perfluoro-2-butyl-tetrahydrofuran (FC 75, PCR/SCM) were instilled into the lungs of one rat through the tracheal cannula. Respiration became regular, and the respiratory rate increased slightly. The rat's color became a normal pink, and the animal's recovery was uneventful.

The second rat received a dose of 6 ml/kg perfluoro-2-butyl-tetrahydrofuran. Respiration became regular, and the rat's color became normal. For the first five hours this animal appeared normal, but at seven hours the rat was showing renewed signs of respiratory distress including labored and irregular breathing. Oxygen was administered for an additional five hours but did not appear to reduce the rat's distress.

The rat was sacrificed and a venous blood sample recovered before necropsy. The lungs appeared redder than normal but not hyperinflated. The left superior lobe was similar in color to the liver and did not inflate like the other lobes when air was infused. The blood $pCO_2$ was 101.2 mm Hg, pO2 was 45.2 mm Hg and the pH was 7.008.

The perfluorophenanthrene treated rat recovered fully. Three days later the rat's breath was analyzed by electron capture detector gas chromatography. As expected, most of the perfluorotetrahydrofuran had evaporated and the perfluorotetrahydrofuran to perfluorophenanthrene was 1/2,301 while the ratio in the instilled mixture was 10,000/1.

This experiment demonstrates that a perfluorocarbon mixture is an effective way to administer a very small, but effective, dose of a very low vapor pressure perfluorocarbon. Upon initial administration of the mixture both the higher vapor pressure and the very low vapor pressure perfluorocompounds were effective in carrying oxygen and substituting for the natural lung surfactant.

The higher vapor pressure perfluorocarbon evaporated so quickly that there was no danger of developing HLS. Within a few hours, well before the natural lung surfactant could be replaced biologically, all but ineffective traces of the higher vapor pressure perfluorocarbon had evaporated.

In the second rat that received only the higher vapor pressure fluorocarbon respiratory distress caused by surfactant shortage returned as soon as the higher vapor pressure fluorocarbon had evaporated (5–7 hours). The blood gas measurements and the lung appearance were consistent with this explanation. On the other hand, in the first rat, after the higher vapor pressure perfluorocarbon had evaporated, the vital surfactant duties were carried out by a thin coating (less than 0.006 ml/kg) of perfluorophenanthrene.

This mixture technique can be readily used to apply thin and effective coatings of perfluorocarbons with extremely low vapor pressures. These materials are generally so viscous, rather like honey, that they cannot be applied by ordinary techniques. It would be expected that these compounds would reside in the lungs essentially for the life of the recipient.

A successful mixture need only contain two fluorocarbons that do not cause any lung or other damage. While the example shown combined a higher vapor pressure perfluorocarbon with a safe very low vapor pressure perfluorocarbon, the invention also contemplates a mixture of two different very low vapor pressure perfluorocarbons with different boiling points. For example, a mixture might contain an effective dose of perfluorophenanthrene (boiling point about 215° C.) with perfluorotetramethylcyclohexane (boiling point about 150° C.) as a carrier. Here the higher boiling compound would persist almost indefinitely as a thin effective coating. The lower boiling compound would evaporate more rapidly but would probably last for a few days rather than a few hours as in the case of perfluoro-2-butyl-tetrahydrofuran.

In addition, an emulsion made with a mixture of higher vapor pressure and very low vapor pressure perfluorocarbons can be easily adapted to combine the advantages of Example 6 with those of Example 8. This would afford superior distribution within the lungs with the use of a smaller volume of the higher vapor pressure perfluorocarbon.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A method of assisting respiration of a mammal having a lung disorder wherein lung surfactant or lung flexibility is inadequate to allow normal respiration so that the mammal can breathe normally using ambient gas without mechanical assistance, the method comprising the step of instilling a liquid mixture through the trachea of said mammal in sufficient quantity to coat alveolar sacs of lungs of said mammal, said liquid mixture comprising a high vapor pressure perfluorocarbon with a boiling point at or below 140° C. at standard atmospheric conditions, selected so that the high vapor pressure perfluorocarbon evaporates from the lungs before significantly diffusing into lung tissue and before causing any hyperinflation of the lung and a minimum effective quantity, said effective quantity being less than 0.1 ml/kg of body weight, of a low vapor pressure liquid perfluorocarbon having a boiling point of at least 150° C. at standard atmospheric conditions and being permeable to ambient gas for spreading to coat inside surfaces of and to persist within said alveolar sacs without inducing hyperinflated lung syndrome, thereby enabling said mammal to breathe said ambient gas without mechanical assistance and with essentially normal $O_2/CO_2$ blood gas exchange.

2. The method of claim 1, wherein said liquid mixture comprises an aqueous emulsion of the high vapor pressure perfluorocarbon and the low vapor pressure perfluorocarbon in a physiologically compatible aqueous medium.

3. The method of claim 2, wherein the emulsion further comprises an effective quantity of a physiologically compatible surfactant.

4. The method of claim 2, wherein said liquid mixture is instilled in quantities between about 1 ml/kg and 20 ml/kg bodyweight.

5. The method of claim 1, wherein said low vapor pressure liquid perfluorocarbon is selected from the group consisting of perfluorophenanthrene, perfluorotetramethylcyclohexane, perfluoromethyldecalin, perfluorodimethylethylcyclohexane, perfluorodimethyldecalin, perfluorodiethyldecalin, perfluoromethyladamantane, perfluorodimethyladamantane, and perfluoro-6,7-H-undec-6-ene, or a mixture thereof.

6. The method of claim 1, wherein said high vapor pressure liquid perfluorocarbon is selected from the group consisting of perfluorohexane, perfluoro-2-butyl-tetrahydrofuran, a perfluoropolypropoxy ether, perfluorotrimethylcyclohexane, perfluoro-5,6-H-dec-5-ene and perfluorodecalin or a mixture thereof.

7. The method of claim 1, wherein said lung disorder is a lung surfactant deficiency.

8. The method of claim 1, wherein said lung disorder is hyperinflated lung syndrome.

9. The method of claim 1 further comprising the step of instilling an effective dose of high vapor pressure liquid perfluorocarbon having a boiling point at or below about 140° C. at standard atmospheric conditions to dissolve and redistribute the low vapor pressure liquid perfluorocarbon previously instilled.

10. The method of claim 9, wherein said effective dose ranges between about 1 ml/kg and 20 ml/kg bodyweight.

11. The method of claim 9 further comprising an additional step following said step of instilling an effective dose of high vapor pressure liquid perfluorocarbon, said additional step comprising broncheo-alveolar lavage with and removal of said effective dose of high vapor pressure liquid perfluorocarbon so that the dissolved low vapor pressure liquid perfluorocarbon previously instilled is removed from the lungs.

12. A method of assisting respiration of a mammal having a lung disorder wherein lung surfactant or lung flexibility is inadequate to allow normal respiration so that the mammal can breathe normally using ambient gas without mechanical assistance by instilling an aqueous emulsion through the trachea of said mammal in sufficient quantity to coat alveolar sacs of lungs of said mammal, said aqueous emulsion comprising:

a minimum effective quantity of a low vapor pressure liquid perfluorocarbon having a boiling point of at least 150° C. at standard atmospheric conditions and permeable to ambient gas for spreading to coat inside surfaces of and to persist within said alveolar sacs without inducing hyperinflated lung syndrome, the minimum effective quantity being less than about 0.1 ml/kg of bodyweight;

a physiologically compatible aqueous medium; and an effective quantity of a physiologically compatible surfactant, thereby enabling said mammal to breathe said ambient gas without mechanical assistance and with essentially normal $O_2/CO_2$ blood gas exchange.

13. The method of claim 11, wherein said physiologically compatible surfactant is selected from the group consisting of a bile salt, a phospholipid, a polyoxylene surfactant, a perflurocarbon ether surfactant and a natural lung surfactant.

14. The method of claim 12, wherein said aqueous emulsion is instilled in quantities between about 1 ml/kg and 20 ml/kg bodyweight.

15. The method of claim 12, wherein said very low vapor pressure liquid perfluorocarbon is selected from the group consisting of perfluorophenanthrene, perfluorotetramethylcyclohexane, perfluoromethyldecalin, perfluorodimethylethylcyclohexane, perfluorodimethyldecalin, perfluorodiethyldecalin, perfluoromethyladamantane, perfluorodimethyladamantane and perfluoro-6,7 H-undec-6-ene, or a mixture thereof.

16. The method of claim 12 wherein said low vapor pressure liquid perfluorocarbon is first mixed with a larger volume of a high vapor pressure perfluorocarbon as a carrier before forming the aqueous emulsion, said high vapor pressure liquid having a boiling point below about 140° C. at standard atmospheric conditions and selected so that the high vapor pressure liquid perfluorocarbon has evaporated from the lungs before significantly diffusing into lung tissue and before causing any hyperinflation of the lung.

17. The method of claim 16, wherein said high vapor pressure liquid perfluorocarbon is selected from the group consisting of perfluorohexane, perfluoro-2-butyl-tetrahydrofuran, a perfluoropolypropoxy ether, perfluorotrimethycyclohexane, perfluoro-5,6-H-dec-5-ene, and perfluorodecalin.

18. A method of assisting respiration of a mammal having a lung disorder wherein lung surfactant or lung flexibility is inadequate to allow normal respiration so that the mammal can breathe normally using ambient gas without mechanical assistance by instilling a liquid mixture through the trachea of said mammal in sufficient quantity to coat alveolar sacs of lungs of said mammal, said liquid mixture comprising:

an effective quantity, less than about 0.1 ml/kg bodyweight, of perfluorophenanthrene for spreading to coat inside surfaces of and for persisting within said alveolar sacs without inducing hyperinflated lung syndrome; and a larger volume of perfluoro-2-butyl-tetrahydrofuran as a carrier for ensuring coating of the lungs, said carrier selected so that the carrier evaporates from the lungs before significantly diffusing into lung tissue and before causing any hyperinflation of the lung, thereby enabling said mammal to breathe said ambient gas without mechanical assistance and with essentially normal $O_2/CO_2$ blood gas exchange.

19. The method of claim 18, wherein said liquid mixture is instilled in quantities between about 1 ml/kg and 20 ml/kg bodyweight.

20. The method of claim 18, wherein a liquid perfluorocarbon selected from the group consisting of perfluorotetramethylcyclohexane, perfluoromethyldecalin, perfluorodimethylethylcyclohexane, perfluorodimethyldecalin, perfluorodiethyldecalin, perfluoromethyladamantane, perfluorodimethyladamantane, and perfluoro-6,7-H-undec-6-ene, or a mixture thereof is used in place of said perfluorophenanthrene.

21. The method of claim 18, wherein a liquid perfluorocarbon selected from the group consisting of perfluorohexane, a perfluoropolypropoxy ether, perfluorotrimethycyclohexane, perfluoro-5,6-H-dec-5-ene, and perfluorodecalin is used in place of said perfluoro-2-butyl-tetrahydrofuran.

22. The method of claim 18, wherein perfluorotetramethylcyclohexane is used in place of the perfluoro-2-butyl-tetrahydrofuran.

23. A method of removing an effective dose of a low vapor pressure liquid perfluorocarbon that has previously been instilled into the lungs of a mammal, the method comprising the steps of:

instilling an effective dose of a high vapor pressure liquid perfluorochemical having a boiling point at or below about 140° C. at standard atmospheric conditions to dissolve the low vapor pressure liquid perfluorocarbon; and removing the high vapor pressure perfluorocarbon as a broncheoalveolar lavage before it has evaporated.

24. The method of claim 23, wherein said effective dose ranges between about 1 ml/kg and 20 ml/kg bodyweight.

25. A method for ensuring normal respiration and ameliorating or preventing lung damage in a mammal that is in receipt of an intravascular administration of a perfluorocarbon-based blood substitute containing an emulsion of a first perfluorocarbon with a boiling point at or below 140° C., the method comprising administering intratracheally to said mammal an effective dose of a second perfluorocarbon to reside in the lungs of said mammal at least until the first perfluorocarbon has dissipated from the mammal, the second fluorocarbon having a boiling point of at least 150° C.

26. The method of claim 25 where the second perfluorocarbon is administered prior to the first perfluorocarbon.

27. The method of claim 25 where the second perfluorocarbon is administered simultaneously with or after the first perfluorocarbon.

28. The method of claim 25, wherein the second perfluorocarbon is selected from the group consisting of perfluorophenanthrene, perfluorotetramethylcyclohexane, perfluoromethyldecalin, perfluorodimethylethylcyclohexane, perfluorodimethyldecalin, perfluorodiethyldecalin, perfluoromethyladamantane, perfluorodimethyladamantane, and perfluoro-6,7-H-undec-6-ene, or a mixture thereof.

29. The method of claim 28, wherein the low vapor pressure perfluorocarbon is selected from the group consisting of perfluorophenanthrene, perfluoromethyldecalin, perfluorodimethylethylcyclohexane, perfluorodimethyldecalin, perfluorodiethyldecalin, perfluoromethyladamantane, perfluorodimethyladamantane, and perfluoro-6,7-H-undec-6-ene, or a mixture thereof.

30. A method of assisting respiration of a mammal having a lung disorder wherein lung surfactant or lung flexibility is inadequate to allow normal respiration so that the mammal can breathe normally using ambient gas without mechanical assistance, the method comprising the step of instilling a liquid mixture through the trachea of said mammal in sufficient quantity to coat alveolar sacs of lungs of said mammal, said liquid mixture comprising perfluorotetramethylcyclohexane as a diluent and a minimum effective quantity, said effective quantity being less than 0.1 ml/kg of body weight, of a low vapor pressure liquid perfluorocarbon having a boiling point of at least 150° C. at standard atmospheric conditions and being permeable to ambient gas for spreading to coat inside surfaces of and to persist within said alveolar sacs without inducing hyperinflated lung syndrome, thereby enabling said mammal to breathe said ambient gas without mechanical assistance and with essentially normal $O_2/CO_2$ blood gas exchange.

* * * * *

UNITED STATES PATENT AND TRADEMARK OFFICE
CERTIFICATE OF CORRECTION

PATENT NO. : 5,824,703
DATED : October 20, 1998
INVENTOR(S) : Leland C. Clark, Jr It is certified that error appears in the above-identified patent and that said Letters Patent is hereby corrected as shown below:

Column 2, line 10, after "lungs.", insert --Id.--.

Column 2, line 20, after "impossible.", insert --Id.--.

Column 2, line 23, after "developed.", insert --Id.;--.

Column 2, line 23, "Tüt üncü" should be one word.

Column 6, line 44, after "140", delete "°".

Column 13, line 7, "tine" should be --time--.

Column 18, line 57, "11" should be --12--.

Column 20, line 54, "150° C." should be --150°C--.

UNITED STATES PATENT AND TRADEMARK OFFICE
CERTIFICATE OF CORRECTION

PATENT NO. : 5,824,703
DATED : October 20, 1998
INVENTOR(S) : Leland C. Clark, Jr It is certified that error appears in the above-identified patent and that said Letters Patent is hereby corrected as shown below:

Column 19, line 4, "perfluoro-6,7 H-undec-6-ene" should be --perfluoro-6,7-H-undec-6-ene--.

Column 19, line 18, "perfluorotrimethycyclohexane" should be --perfluorotrimethylcyclohexane--.

Column 19, line 54, "perfluorotrimethycyclohexane" should be --perfluorotrimethylcyclohexane--.

In Fig. 1 on sheet 1 of 4, "RERIOD" should be --PERIOD--.

Signed and Sealed this

Nineteenth Day of September, 2000

Attest:

Q. TODD DICKINSON

Attesting Officer     Director of Patents and Trademarks